(12) United States Patent
Wu

(10) Patent No.: US 9,617,191 B1
(45) Date of Patent: Apr. 11, 2017

(54) BIOREACTOR SYSTEM AND METHOD

(71) Applicant: Xianggen Wu, Mississauga (CA)

(72) Inventor: Xianggen Wu, Mississauga (CA)

( * ) Notice: Subject to any disclaimer, the term of this patent is extended or adjusted under 35 U.S.C. 154(b) by 0 days.

(21) Appl. No.: 15/178,261

(22) Filed: Jun. 9, 2016

(51) Int. Cl.
| C05F 17/02 | (2006.01) |
| C12M 1/00 | (2006.01) |
| C12M 1/34 | (2006.01) |
| C12M 1/06 | (2006.01) |
| C12M 1/12 | (2006.01) |

(52) U.S. Cl.
CPC ........ *C05F 17/027* (2013.01); *C05F 17/0258* (2013.01); *C05F 17/0282* (2013.01); *C12M 23/34* (2013.01); *C12M 25/16* (2013.01); *C12M 27/08* (2013.01); *C12M 29/06* (2013.01); *C12M 41/12* (2013.01)

(58) Field of Classification Search
CPC ...... C12M 23/34; C12M 25/16; C12M 27/08; C12M 29/06; C12M 41/12
See application file for complete search history.

(56) References Cited

U.S. PATENT DOCUMENTS

| 4,212,949 | A | * | 7/1980 | Kozhemyakin | ........ C12M 23/04 435/294.1 |
| 4,302,545 | A | * | 11/1981 | Redikultsev | ........... B01D 19/02 435/286.1 |
| 4,668,632 | A | * | 5/1987 | Young | ................... C12M 29/06 210/220 |
| 5,043,431 | A | * | 8/1991 | Pungor, Jr. | ............. C12M 47/02 530/399 |
| 5,187,095 | A | * | 2/1993 | Bliem | .................... C12M 29/04 435/299.1 |
| 5,744,351 | A | * | 4/1998 | Bryan-Brown | ..... C05F 17/0205 366/244 |
| 6,592,751 | B2 | * | 7/2003 | Haridas | ................... C02F 3/282 210/120 |
| 7,718,057 | B2 | * | 5/2010 | Jordan | .................... C02F 3/085 210/150 |
| 8,306,665 | B2 | * | 11/2012 | Tsangaris | ............... C03B 5/005 422/105 |
| 2012/0052578 | A1 | * | 3/2012 | Kauling | ................. A61K 38/12 435/383 |

(Continued)

*Primary Examiner* — Gautam Prakash
(74) *Attorney, Agent, or Firm* — Nasser Ashgriz; UIPatent Inc

(57) ABSTRACT

The present invention is a composting bioreactor system that can be continually fed with biodegradable solid wastes, waste waters and exhaust gases, that can automatically recycle the biodegradable wastes into liquid nutrients and heat energy, and that automatically supplies the nutritious liquid and heat into the integrated hydroponics system or aquaponics system. The invention together with the integrated food growing system can be installed onsite in places such as household balconies, household backyards and premises of restaurants and food factories etc. therefore can lead to zero mileage targets both for recycling the wastes and for growing the foods consumed in the same location. It can fully recover and reuse all the nutrients and heat energy from the treated wastes. It can also reach the target of nearly zero pollution to the environment during all processes. For better operational efficiency, an oblique cone agitator, a fish plow agitator and a vortex flower turbine are specially designed for the bioreactor system.

14 Claims, 14 Drawing Sheets

(56) References Cited

U.S. PATENT DOCUMENTS

| | | | | |
|---|---|---|---|---|
| 2012/0097607 A1* | 4/2012 | Merai | ................. | C02F 3/04 |
| | | | | 210/609 |
| 2013/0078708 A1* | 3/2013 | Roux Dit Buisson | . | C12M 21/02 |
| | | | | 435/257.1 |
| 2015/0279618 A1* | 10/2015 | Peters | ................ | B01J 19/085 |
| | | | | 250/453.11 |

* cited by examiner

BIOREACTOR SYSTEM AND METHOD

FIELD OF THE INVENTION

This invention relates to systems for treatment of biodegradable wastes by way of aerobic and anaerobic decomposition. More specifically, this invention relates to composting bioreactor systems that can be continually fed with biodegradable solid wastes, waste waters, and exhaust gases and that automatically recycle the fed wastes into liquid nutrients and heat to grow foods.

BACKGROUND OF THE INVENTION

Biodegradable waste is the type of waste that can be broken down by way of composting (aerobic decomposition and anaerobic decomposition) into base compounds ($H_2O$, $CO_2$, compounds of Nitrogen, Phosphorus, Potassium and others), energy (heat) and residual humus. The residual humus can eventually break down into fine particles and can be automatically transported by water circulation.

Biodegradable wastes are produced in huge volume from human activities. They include solid wastes such as kitchen food wastes and backyard plant wastes as well as packaging wastes (papers, cartons and wood pallets etc.), waste waters such as from sinks of kitchen and from sinks, showers, bathtubs as well as toilets of bathroom, and exhaust gases such as from furnace vent and stove vent. Households and industries in agriculture, restaurant and food production, etc. are all producers of the wastes.

It is a labour burden task to collect the wastes from households and industries and to transport them into municipal treatment centers. Producers of the wastes also need to spend time and labor to get them ready to be collected. Greenhouse gas emission from transportation of the wastes and the recycled result products such as compost is one of the inputs leading to climate change. It costs a lot of money from both private and public in building and maintaining the urban sewage piping systems for transporting the waste waters into municipal treatment centers. Exhaust gases discharged directly into atmosphere without treatment from households and industries increase air pollutions.

Recycling the above wastes in the municipal treatment centers by way of composting, incineration or landfill etc. can recover some part of the beneficial ingredients from the wastes treated, but also pollutes the atmosphere, soil and even groundwater. Furthermore, it also needs large lands and costs a lot in building and maintaining the treatment utilities.

A lot of efforts have been made in addressing treatment of the biodegradable wastes within the source location. Composters including vermi-composters that use natural ventilation are not in a sealed vessel therefore let go heat, odors and exhaust gases into the atmosphere.

The patent number U.S. Pat. No. 5,744,351 to Michael Bryan-Brown discloses a bioreactor for aerobically composting organic waste inside a sealed container. It integrates a mixing assembly and an aeration system so that the composting wastes can be ventilated inside the container. However, this design type needs to manage the exhaust gases by way of a bio-filter and to manage the leachate liquid by use of a pump.

The patent application No. CN101823069 by Aimin Li et al discloses an auto-controlled composter with ventilation and heat components to promote the composting processes inside the vessel. Again it still needs components to filter the exhaust gases and to manage the leachate liquid.

Both the above composters are designed for the purpose to recycle the bio wastes into compost only. The bio wastes are fed by batch into the composter, after certain time the completed compost is to be discharged and transported. Pollutants to environment can be disposed from the exhaust gases, the leachate liquid and the completed compost. Nutrients of the bio wastes and heat from the composting wastes are not fully utilized. When these composters are employed, the bio wastes inside the vessel of a batch undergo all the composting stages, therefore the quantity of microorganisms of each stage reaches its highest point at its stage and then decreases or even disappears in other stages because of changed conditions. When the complete compost of the batch is discharged, the microorganisms inside the composter are also discharged. It is a total new process for microorganisms to grow into large quantities during the new composting stages of the newly fed batch of bio wastes.

It is desirable that the biodegradable wastes be composted within its source location with the completed compost locally used with zero mile of transportation, with zero pollution to the environment from the composting processes, and with all the nutrients and heat energy from the wastes fully recovered and reused. It is also desirable that the condition of microorganisms stay unchanged when the biodegradable wastes undergo each of the composting stages.

In response to the growth of demand for healthy foods available in minimum mileage, the hydroponics system and the aquaponics system have been in practice for decades. When these practices happen in the household backyard or in the food consume premises, zero food mileage can be achieved as regard to the foods produced and consumed in the same location.

However, the conventional hydroponics system needs to add artificial nutrients into the circulating water to feed the plants. In the typical aquaponics system, fish feed is from outside source, and the waste water from integrated fishing tanks doesn't have enough nutrients to support the growing plants, therefore minerals and other nutrients have to be added. Furthermore, a filter and a bioreactor are required to separate and to degrade the solid wastes in the waste water from the aquaponics fish tanks.

However, one can use, for instance, compost tea to supply nutrients. Compost tea is produced by putting a bag of compost into a vessel with aerated water for certain time to allow microbes grow. It is nutritious for feeding plants and therefore good to be added into the hydroponics and aquaponics systems. Different devices are available but are separately operated.

Although it is valuable to grow short mileage foods with little water loss by way of the hydroponics system or the aquaponics system, their values are limited by the high start-up costs comparing to the volume of foods produced, for they are used to grow foods only. The systems do not have the function to automatically recycle the waste biomass produced from the systems and other sources.

It is desirable to have a bioreactor system that can be integrated into the hydroponics system or the aquaponics system, which can onsite automatically recycle biodegradable wastes into nutrient liquid to feed the growing plants, and that can also grow feed for the aquarium animals. Furthermore, it is desirable to have a bioreactor system that can be integrated into the food growing systems, that can automatically recycle all the biodegradable wastes including solid wastes, waste waters and exhaust gases from both the food production sources and from the onsite human activities, and that can fully recover nutrients and heat energy from the treated wastes to produce foods with zero pollution to the environment.

The patent application No. CA2759981A1 by Nicholas Hermes and James Sawada discloses a food production system that composts biomass and uses the completed compost to grow foods with heat and nutrients recovery. In this system biomasses are fed by batch mode to a composter and then physically transferred into another invertebrate culture unit and lastly transferred into a food culture unit. The heat recovery is carried by way of a complicated pipe system which circulates heat exchange liquid. In this design, the biomass is not kept inside of a sealed vessel during all processes; pollutants to environment can be disposed from the exhaust gases while nutrients and heat are not fully recovered.

In the prior art composters that can be employed onsite of the waste source, the biomasses or the bio wastes or the organic wastes or the biodegradable wastes that can be fed into the composter, have numerous limitations. The wastes such as wood pallets, tree trunks and branches of large size are usually not acceptable. The present invention provides an onsite biomass composting and reuse, which overcomes all the limitations of the prior art.

One of the important steps for sealed in-vessel composting is to mix or agitate the inside contents so that all the volume is well aerated. Either a slow speed motor that rotates the whole vessel/drum or a high speed motor that drives an agitator to cause movements of the whole volume is usually employed. In the U.S. Pat. No. 5,744,351, a vertically installed slidable mixing assembly is employed so that almost all the inside volume can be reached for agitation. This method requires a worker to manually operate the mixing assembly. In the patent application CN101823069, a mixing module is horizontally installed and it horizontally rotates the whole volume inside the vessel. All these methods are not efficient in comparing the power energy required with the simple aeration resulted.

The traditional plow is typically much more efficient in comparing the power required with the volume of mass (soil) moved. Inside a sealed vessel, if some part of the contents along the bottom layer is physically moved, it can cause somewhat movements of the whole contents. This kind of movements are good enough for aeration of the whole volume, especially if the air is from a space below the volume. Desirably a very slow speed of movements caused by rotating a plow type agitator inside the lower layer of the volume can well aerate the whole volume.

Also, most prior art agitators for in-vessel liquid agitation are designed for high speed rotation movements that cause movements of the whole volume. During very slow rotation, the volume and the dimensional range moved by these agitators are very limited therefore can not reach good agitation effects. It is desirable to have a specially designed liquid agitator that can reach better agitation effects from slow speed rotation, especially for the concaved or conical volume in which the height gradually decreases from the middle point to the side wall point.

One of the methods to heat greenhouse is to use a rocket stove by burying the chimney tube in ground to hold heat from the circulating combustion smoke underground. This is a right way to "degrade" by burning large branches and tree trunks which cannot be acceptable to the onsite composter. But this method causes exhaust gas emission because the combustion smoke goes directly into the atmosphere.

Studies have been applied in treatment of wastewater by using the Microbial Fuel Cell (MFC) technology. MFCs consume by microorganism organic matter of the waste water to produce electricity and therefore speed the treating processes of waste water. Temperature is one of the factors that affect the efficiency for MFCs to produce electricity.

In recycling the bio-degradable wastes into good staff for growing uses, the prior arts tend to deal the processes separately therefore don't solve the problem in high efficiency and even cause problems to each other. The apparatuses designed to treat solid wastes take the leachate liquid and exhaust gases as extra burdens which have to be specially managed. The apparatuses designed to treat waste waters take the solids inside as extra burdens which have to be specially managed. The apparatuses designed to treat exhaust gases have to employ liquid and solid filter media. The apparatuses designed to produce compost tea have to create conditions to grow microorganisms from the completed compost in which most of the microorganisms are not in the best state of activity and quantity. The apparatuses designed for vermi-composting have to manage the humidity of the fed solid waste, and the fed waste has to undergo a first stage of composting before it becomes food for worms. In winter we need to buy fire woods or gas to heat a green house while we put a lot of staff that is good for heating by burning into garbage bins that causes a lot afterward works to have it treated somewhere far away.

In the patent application US 2007/0059819A1, Stephen Storch discloses an apparatus for brewing compost tea which is composed of a plurality airlift pumps for agitation and aeration. This design causes a vortex swirl circulation in the tank. Most of the nowadays apparatuses used for brewing compost tea have employed this technique, however, in all the apparatuses the vortex swirling is created for agitation and aeration only, the kinetic energy of the vortex swirling is not harnessed for use.

It is desirable to have an integrated system that has functions of all the above mentioned prior art apparatuses and that can make every burden into good use. It is further desirable that the kinetic energy from the vortex swirling can be harnessed for uses in an integrated system such as mixing and agitating the solid wastes. It is also desirable to have a specially designed turbine that can harness the kinetic energy from the vortex swirling in high efficiency.

SUMMARY OF THE INVENTION

The present invention is a composting bioreactor system that can be continually fed with biodegradable solid wastes, waste waters and exhaust gases, and that can automatically recycle the biodegradable wastes into liquid nutrients and heat energy. It automatically supplies the nutritious liquid and heat into the integrated hydroponics system or aquaponics system. The invention together with the integrated food growing system can be installed onsite in places such as household balconies, household backyards and premises of restaurants and food factories etc. It can lead to zero mileage targets both for recycling the wastes and for growing the foods consumed in the same location. It can fully recover and reuse all the nutrients and heat energy from the treated wastes. It can also reach the target of nearly zero pollution to the environment during all processes. For better operational efficiency, an oblique cone agitator, a fish plow agitator and a vortex flower turbine are specially designed for the bioreactor system.

The present invention comprises a bioreactor body, an extension, a central control unit and a stove unit. The bioreactor body is an insulated and sealed vessel with two (upper and lower) separators to divide the inside volume into three chambers (the upper chamber, the middle chamber and the lower chamber). It has a mixing agitator module, an aeration module and a heating module installed. Preferably, the aeration module composes a plurality of airlift pumps so that a vortex swirl circulation in the middle chamber is created. The bioreactor body has inlets including waste water inlet(s) and exhaust gas inlet(s) and outlets including liquid outlet(s) and air outlet(s). A feed module on the top lid is cylindrical or other shapes of cross-section. The feed module has a door on each end and the two doors can be interlocked and controlled by an infrared auto-sensor on the top end. Sensors for temperature, humidity, oxygen, ammonia, carbon dioxide and air pressure are installed inside the bioreactor body vessel and connected into the central control unit. The mixing agitator module has a motor installed on top of the bioreactor body lid to drive a shaft rod installed through the lid by way of a bearing, and there fixed on the shaft rod are agitator mechanisms inside the upper chamber and the middle chamber of the vessel.

The extension of the bioreactor system stays inside a wicking bed and works as its water reservoir. It composes an upper channel, a middle channel and a lower channel. When the stove unit is employed it has a heat radiator structure staying under the bioreactor body vessel and works as its support base.

Other objects, features, and advantages of the present invention will be readily appreciated from the following description. The description makes reference to the accompanying drawings, which are provided for illustration of the preferred embodiment. However, such embodiments do not represent the full scope of the invention.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF THE DRAWINGS

Figure 1:
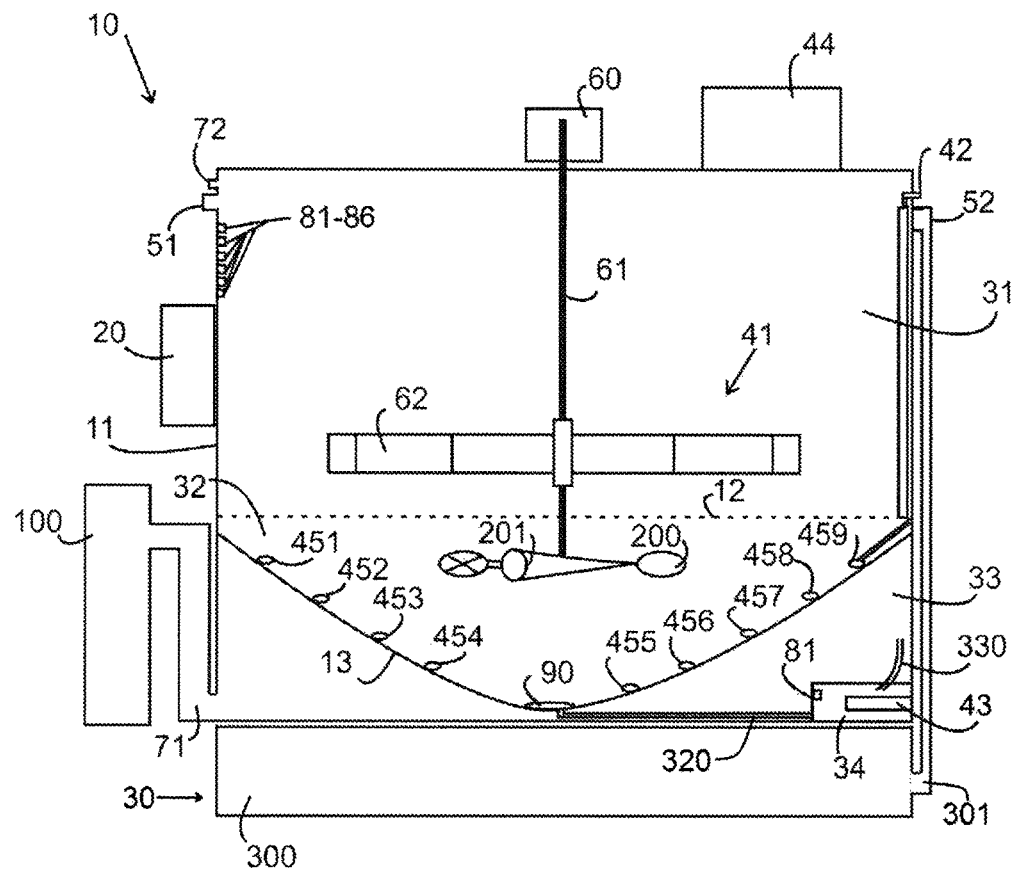
FIG. 1 shows the bioreactor body configured with the aeration module composing perforated pipes and with the motorized mixing agitator module.

As shown in FIG. 1, a composting bioreactor system of the present invention comprises of a bioreactor body 10, an extension 100, a central control unit 20 and a stove unit 30. The bioreactor body 10 has an insulated and sealed vessel 11 with two (upper and lower) separators 12-13 to divide the inside volume of the vessel 11 into three chambers—the upper chamber 31, the middle chamber 32 and the lower chamber 33. The bioreactor body 10 also has a mixing agitator module 41, an aeration module 42 and a heating module 43 installed inside the body vessel 11. The bioreactor body 10 has several inlet ports, including waste water inlet(s) 51 and exhaust gas inlet(s) 52 and outlet ports, including liquid outlet(s) 71 and air outlet(s) 72.

Figure 2:
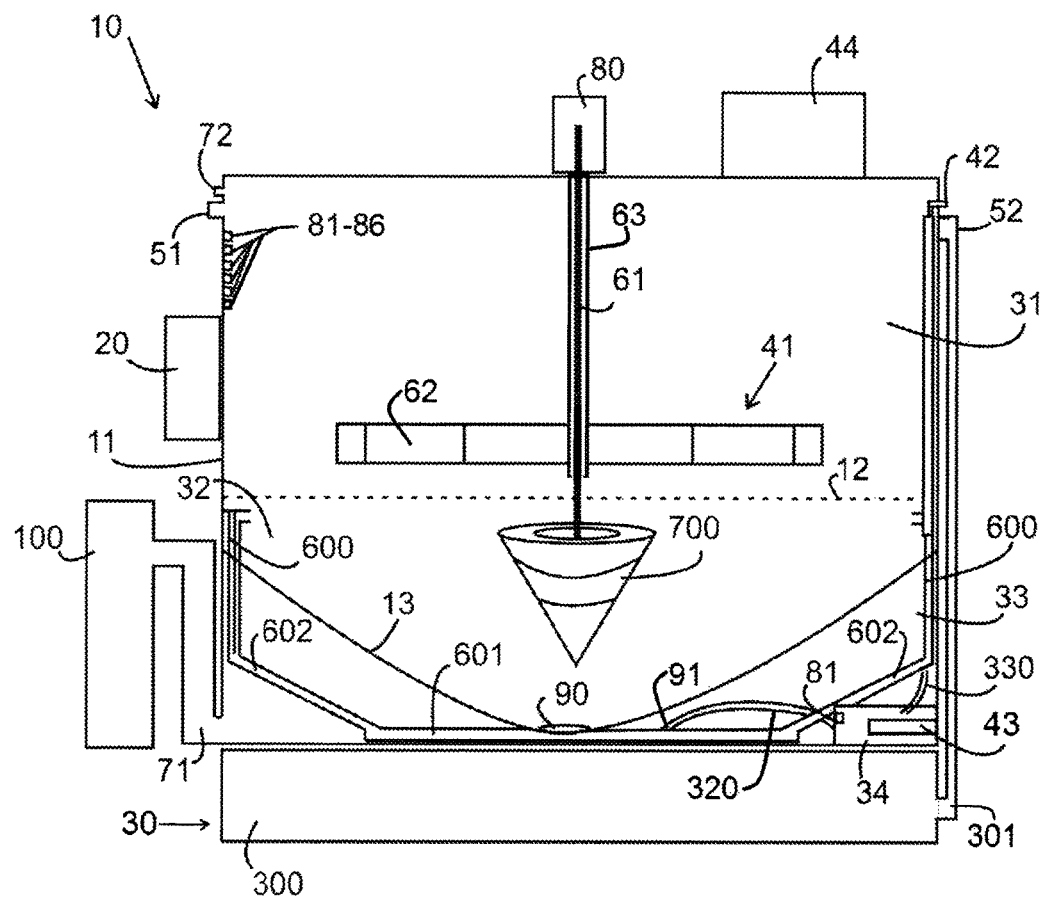
FIG. 2 shows the bioreactor body configured with the aeration module comprising airlift pumps and with the mixing agitator module driven by the vortex flower turbine.
Figure 3:
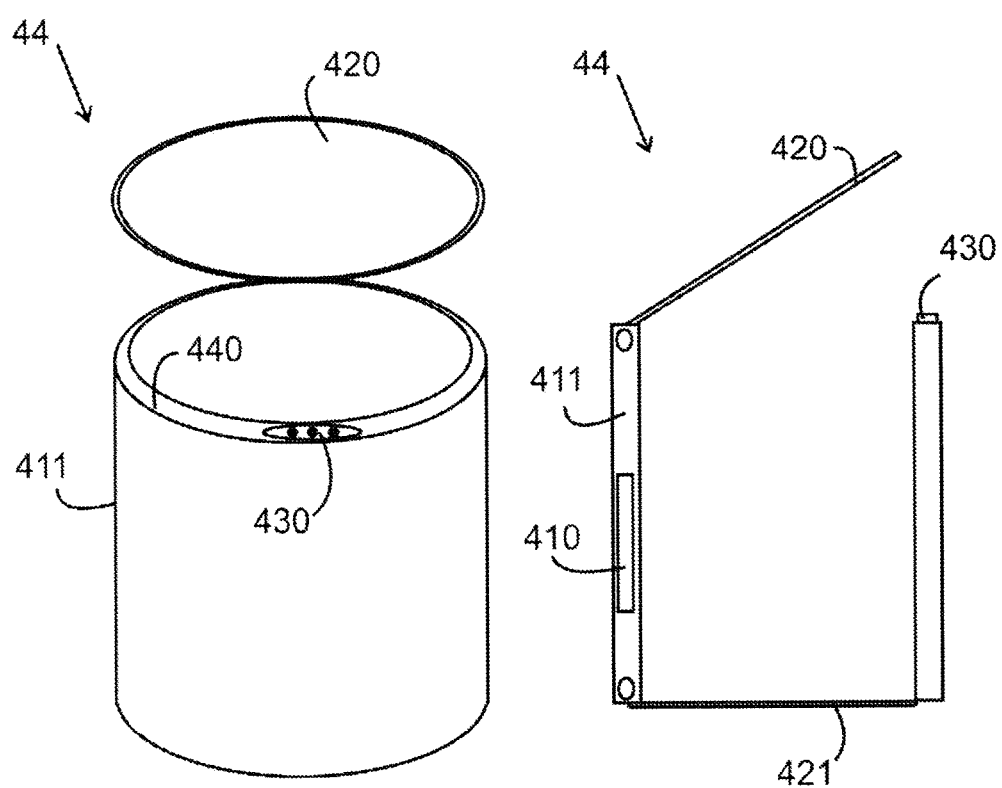
FIG. 3 shows perspective and cross section of a feeding module.

As shown in FIGS. 1-3, the bioreactor body 10 has a feed module 44 on the top lid of the body vessel 11. The feed module 44 is preferably a cylindrical feed port, however, it can have any other cross-sectional shape, such as rectangle or square. The feed module 44 has control circuit 410 inside its side wall 411 and motorized doors 420, 421 on each end. The doors 420, 421 are interlocked and controlled by an infrared auto-sensor 430 on the top end 440. Preferably, at least the bottom door 421 or both doors 420-421 are slide doors or tubular rolling doors, which can be engaged with its slide-way edges to maintain good sealed state when pushed by air pressure from inside the body vessel 11. When the infrared auto-sensor 430 detects thermal human movements the top door automatically opens to allow feeding of wastes. The top door 420 stays open as long as there is a thermal human movement. Once the human movement is not detected for a certain time (for example 2 seconds), the top door 420 automatically closes. Then, the bottom door 421 automatically opens after certain time (for example 3 seconds) to allow the waste inside the feed module 44 to drop into the upper chamber 31 of the vessel 11. The bottom door 421 automatically closes after certain time (for example 3 seconds) after it opens and if the top door 420 is close. The system may also be configured to let the bottom door 421 automatically open if the top door 420 is stayed open for a certain time (for example 5 seconds). This allows continuous feeding of the waste, including waste water, into the upper chamber 31. In this case the bottom door 421 closes at a certain time (for example 3 seconds) after the top door 420 is closed. This function may also be realized by having a specially designed push button on the side wall 411 of the feed module 44 and/or on the central control unit 20. Preferably, the control circuit 410 may be connected into the central control unit 20 to control and monitor the opening and closing of each door from the central control unit 20.

A plurality of sensors 81-86 for monitoring temperature 81, humidity 82, oxygen 83, ammonia 84, carbon dioxide 85 and air pressure 86 are installed inside the bioreactor vessel 11 and are connected to the central control unit 20.

The mixing agitator module 41 has a motor 60 installed on the top of the bioreactor body vessel 11 to drive a shaft rod 61 installed through the lid of the vessel 11 by way of a bearing. Fixed on the shaft rod 61 are an agitator mechanism 62 inside the upper chamber 31 and an agitator mechanism 200 inside the middle chamber 32 of the vessel 11.

The upper separator 12 is a substantially flat perforated board to separate particles with diameters larger than certain size (for example ½-¼ inch). Therefore, the upper separator filters relatively large particles.

The lower separator 13 is a concaved dish or a conical separator, which has a drain 90 at its center (middle lowest part). The liquid from the middle chamber 32 drains into a heating sub-chamber 34, which is located in the lower chamber 33. There is a filter on the top of the drain 90 to separate particles with diameters larger than a certain size (for example ¼-⅛ inch). Clearly, this filter separates smaller particles than that of the upper separator 12. The lower separator 13 is made of thermal conductive material so that the liquid inside the middle chamber 32 exchanges heat with the liquid in the lower chamber 33.

The middle chamber 32 is equipped with an aeration module 42. The aeration module comprises of a series of air pipes 451-459 positioned in circular manner on the upper surface of the lower separator 13. The air pipes are perforated to introduce air into the waste material containing in the middle chamber 32, thus aerating the waste materials both inside the middle chamber 32 and the upper chamber 31.

The liquid collecting in the lower chamber exits the vessel 11 from the liquid outlet port 71. Since the drain 90 is in the middle lowest part of the lower separator 13, it is easy to remove most of the liquid inside body vessel 11 through the liquid outlet 71, especially when the vessel 11 is moved from one spot to a new spot.

The lower chamber 33 has a heating sub-chamber 34. This sub-chamber 34 has a relatively small size (e.g., smaller than 6×6×12 inches) so that it can maintain a high temperature using a small electric heater. The heating sub-chamber 34 is preferably installed on the bottom wall of the vessel 11 and its top and side walls are insulated to prevent heat losses. The liquid exiting the middle chamber 32 through the drain 90 enters the heating sub-chamber 34 by way of the inlet pipe 320. Heated liquid leaves the sub-chamber 34 from an outlet pipe 330 to enter inside the remaining volume of the lower chamber 33. The inlet 320 and outlet 330 pipes for the heating sub-chamber 34 are small-sized (for example with cross-sectional diameter smaller than 3 inches) and have a length of at least ⅓ of the diameter of the vessel bottom so that its inside volume is relatively separated from the middle chamber 32 and from remaining volume of the lower chamber 33. The heating module 43 is installed through the side wall of the bioreactor vessel 11 into the heating sub-chamber 34. Temperature inside the heating sub-chamber reaches 70-100° C. (much higher on the electric heater surface of heating module 43) to kill pathogen microbes and weed seeds etc. of the liquid stream flowing through the heating sub-chamber 34. The liquid in the remaining volume of the lower chamber 33 moderates the high temperature liquid from the heating sub-chamber 34 therefore the liquid introduced into the extension 100 through the liquid outlet 71 of the lower chamber 33 is in a temperature range that is good for plants and worms growing in the wicking bed above the extension 100.

When the stove unit 30 is employed, it is mostly used when the ambient temperature is low. All the volume inside the lower chamber 33 is heated by the stove radiator 300 therefore the heating module 43 runs less. The heat from stove radiator 300 reaches to all contents of the whole body vessel 11 therefore help maintaining a good condition for the composting processes. The heat from stove radiator 300 also reaches into the extension 100 and the integrated growing beds by the water circulation from the lower chamber 33 of the body vessel 11 into the extension 100 and then into the growing beds.

The mixing agitator module 41 may employ any prior art motors and agitator mechanisms that fit for the bioreactor. Preferably, the motor 60 is a slow speed motor (for example less than 10 rpm) so that it consumes less electricity, causes less noise and produces larger torque to rotate the agitator mechanisms 62 and 200.

Preferably, the agitator mechanism 200 inside the middle chamber 32 is composed of a plurality of cones 201 horizontally installed on balanced circle frames 202 so that it can cause more volume of liquid to move by slow rotation and increase the liquid travel distance by each rotation because of the height of the cone 201. Further preferably, it is composed of a plurality of oblique cones 201 made by method as shown in FIGS. 5A-F. It is easier to install the oblique cones 201 made by this method on a horizontal frame surface. When an oblique cone 201 is installed horizontally along its longest ht line the axis of the oblique cone is in a tilted angle (nearer to perpendicular) opposite to the upper surface of the concaved or conical lower separator 13, this angle helps the rotated volume of liquid pushing along the surface harder therefore producing more secondary liquid currents from the rotations.

The oblique cones 201 may be arranged with one or more installation combinations of different 3-dimensional space positions. As shown in FIGS. 5D-F, typically they are serially installed on a circle frame 202 with the line from apex point t to the longest slant height point h horizontally aligning with the lower surface of an arc tangent of the circle frame with at least two points fixed. The longest slant height point h on the base is the most forward top point is therefore named head point of the oblique cone 201. A part near the apex point t of one oblique cone 201 can be arranged inside the part near to the head point h of another neighbored oblique cone 201 so that more oblique cones 201 can be installed on one circle frame 202. One agitator can employ a plurality of circle frames 202 which are horizontally arranged or vertically arranged. When the circle frames 202 are vertically arranged, the diameter of the lower circle frame 202 is smaller than the diameter of the upper circle frame 202 so that the agitator works well above the concaved or conical lower separator 13. When more than one circle frames 202 are employed, the size of oblique cones 201 maybe specially configured for each of the circle frames 202. All oblique cones 201 installed on one agitator are all in the same clockwise or anti-clockwise direction, the same as the rotation direction of the driven motor 60.

Figure 5A:
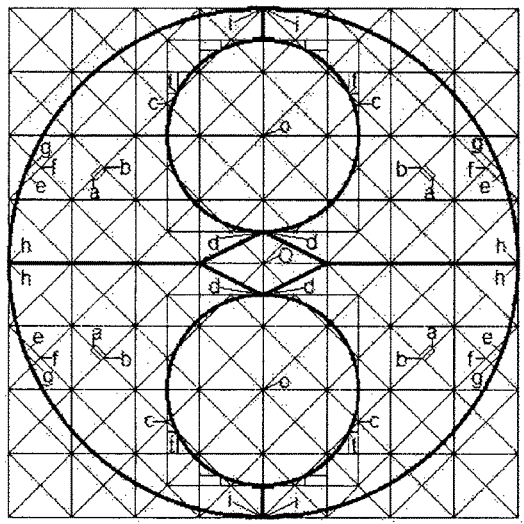
FIGS. 5A-C show geometry drawings and method for making a prototype sample of an oblique cone agitator.
Figure 5B:
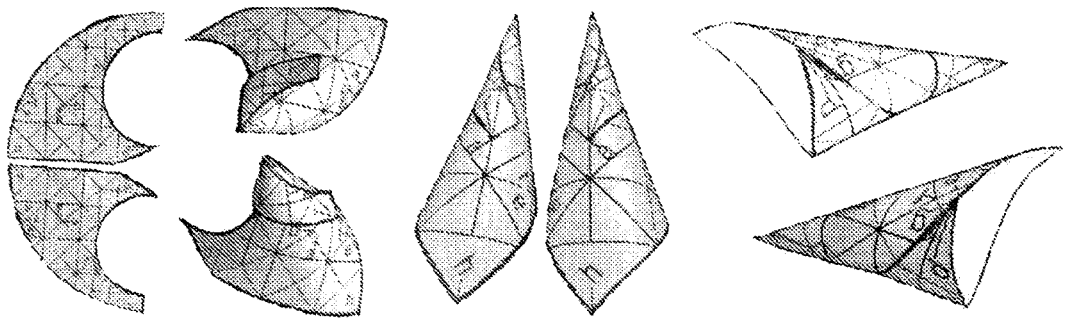

Details for making the oblique cones are showing in FIGS. 5A-B.
  (1) Inside of a circle O draw two equal circles o and a rhombus based on the given spaces and points.
  (2) Find the intersection point t of the inner circle o and the line segment hi which has a part staying inside the inner circle o.
  (3) Based on pint t find the length of the line segment tc and find point a and point e based on the length of tc so that tc=ab=ef.
  (4) Point g is a point on the circle O which is perpendicular to of at point e.
  (5) Harvest the 4 pieces of blades by cutting the thicker lines.

(6) Fold the blade by turning it into opposite directions at the turning point t to form the shape of an oblique cone.
(7) Adjust the shape so that point i coincides with point a and point d coincides with point g.
(8) Point t is referred as apex point and point h is referred as the point which has the longest slant height of the oblique cone.
(9) The area along the line segment ht is relatively flat therefore is good for align with a flat surface of a frame.

When the oblique cone is installed on a circle frame and the line ht is in horizontal level, h is the most forward point therefore is named head point while t is the aftermost point therefore is named tail point. At this position axis of the oblique cone tends to be in an tilted angle near to perpendicular to the opposite concaved or conical surface of the lower separator.

The size of the circle frame 202 depends on both the quantity of oblique cones 201 to be installed and the length in arc tangent of the circle for each cone to occupy on the circle. Since the tangent value of an known angle can be found from a tangent chart, the radius of a circle frame can be calculated according to the Pythagorean Theorem for a given quantity of oblique cones 201 to be installed and a given length in arc tangent for each oblique cone to occupy on the circle frame 202.

Figure 5C:
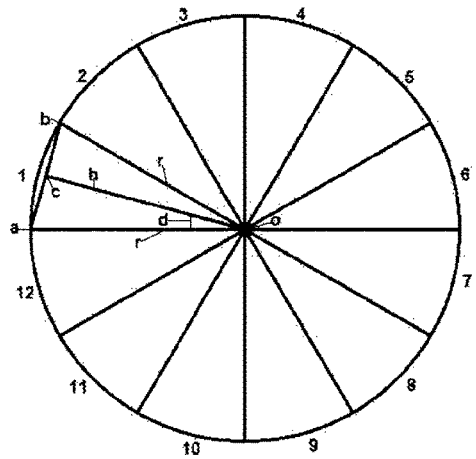
Figures 5D, 5E:
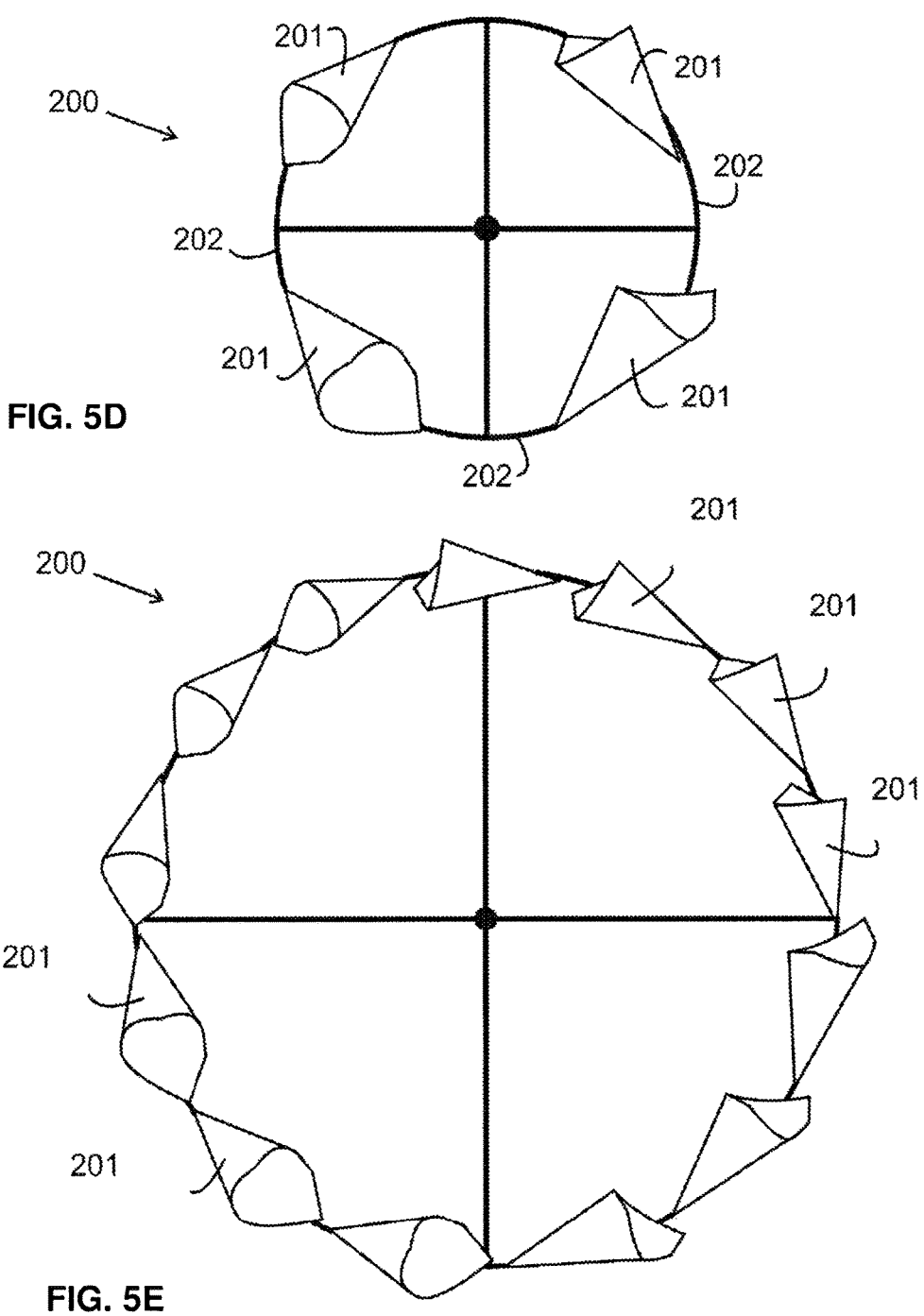
FIGS. 5D-F show method to install oblique cones on circle frames for making an prototype agitator.
Figure 5F:
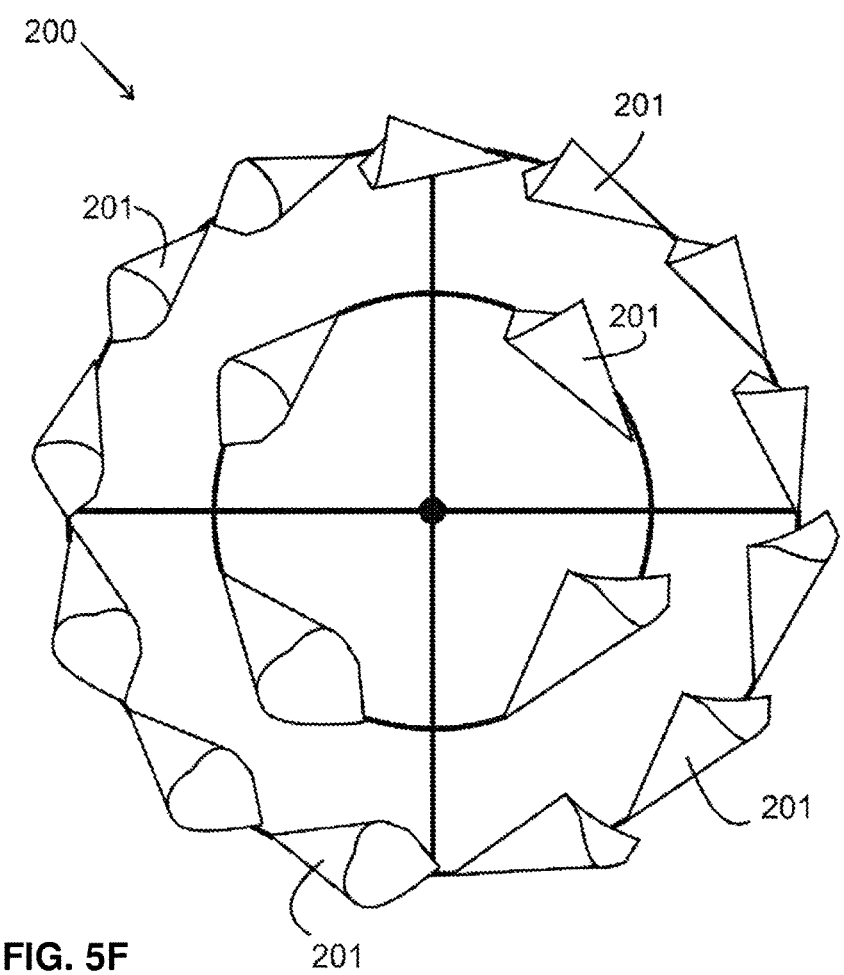

As shown in FIG. 5C:
If the length of arc tangent ab is 10 cm and 12 oblique cones are to be installed,
Then: ac=10/2=5 cm
angle d=1/2(360/12)=15°
tan d=tan 15°=0.26795
Since: tan d=ac/h=5/h,
Then: h(tan d)=5
Therefore: h=5/(tan d)=5/0.26795=18.66
Since: $ac^2+h^2=r^2$,
Then: $r^2=ac^2+h^2=5^2+18.66^2=25+348.1956=373.1956$,
Therefore: r=square root of 373.1956=19.31827 cm.

Figure 5G:
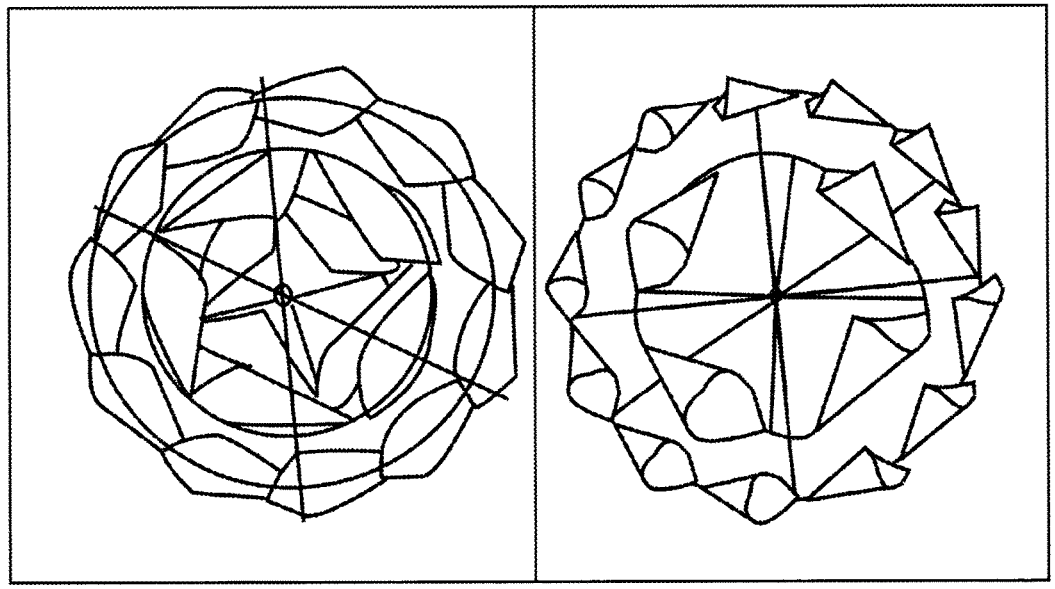
FIG. 5G shows a top view and a bottom view of a prototype sample of an oblique cone agitator comprising 20 oblique cones installed on 3 circle frames in 2 layers.

FIGS. 5D-F shows the method of making prototype oblique cone agitator samples by installing oblique cones 201 on circle frames 202. FIG. 5G are pictures of both a top view and a bottom view of a prototype sample of the agitator that has 20 oblique cones installed on 3 circle frames vertically in two layers. The upper layer has two circle frames in the same horizontal level. On the upper outer circle frame 11 oblique cones are serially installed with some part near to the tail t point of the front oblique cone staying inside the part near to the head h point of the oblique cone immediately after. On the upper inner circle frame 5 oblique cones are serially installed with the tail t of the front cone right contact with the head h of the oblique cone immediately after. On the lower layer circle frame 4 oblique cones are installed of which the ht lines are perpendicular to each other for any two neighboring oblique cones. All the 16 oblique cones on the 2 upper circle frames are of the same size. The 4 oblique cones on the lower circle frame are of a larger size than the cones of the upper layer.

Figure 6A:
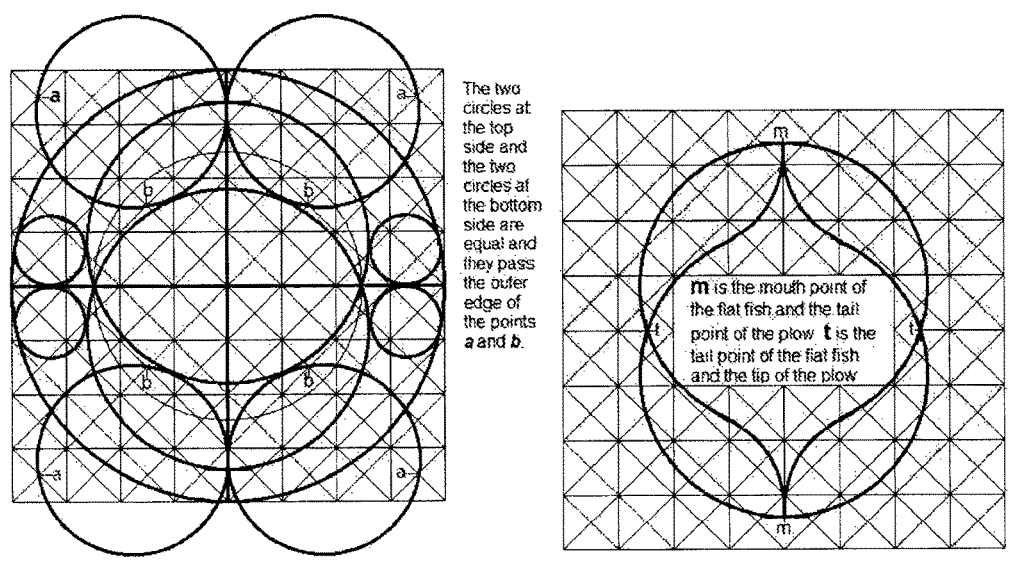
FIG. 6A shows geometry drawings for harvesting 4 fish plow blades from a sheet based on FIG. 7A.
Figure 6B:
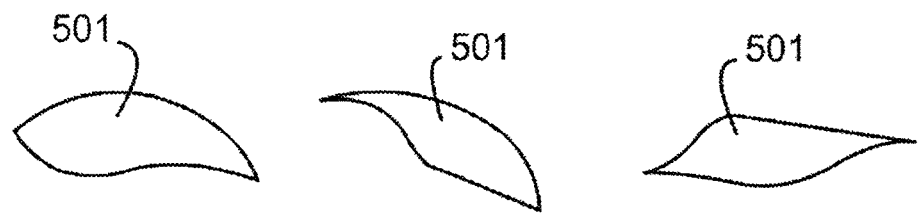
FIGS. 6B-C show method to make a prototype sample of a fish plow agitator.
Figure 6C:
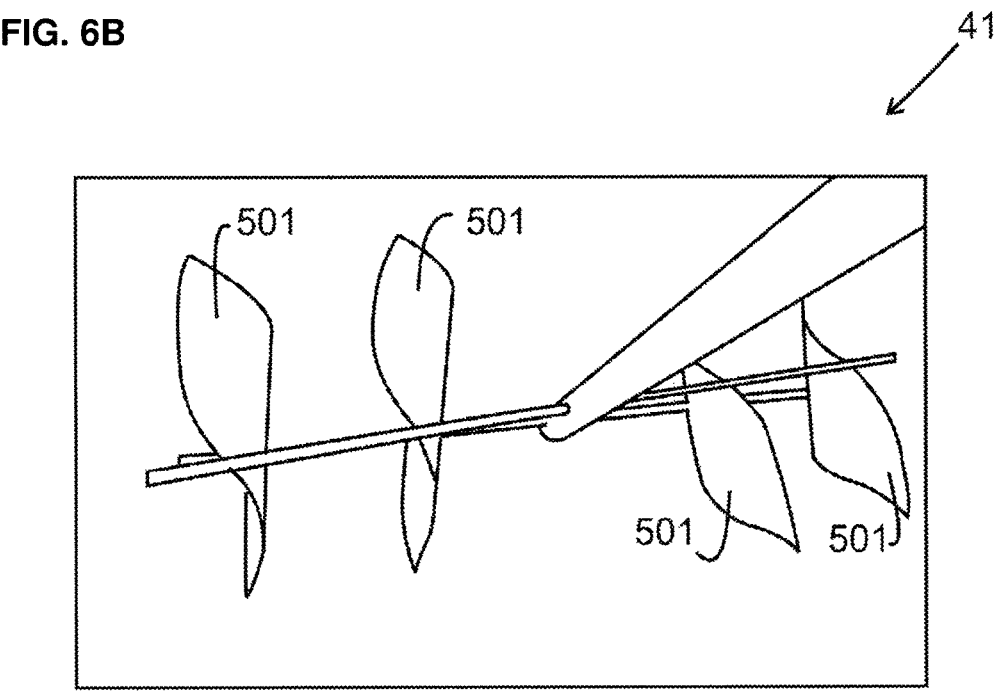

As shown in FIGS. 6A-C, preferably, the agitator mechanism 62 inside the upper chamber 31 is composed of a plurality of specially designed fish plows 501 installed on balanced frames. It is named fish plow agitator because the shape of the flat blade is like a fish, and when the agitator rotates inside the solid waste the movement of the fish plow 501 is someway like a fish swimming inside muddy water and causing movements of the volume around the fish. The 3-dimensional fish plows 501 can be arranged with one or more installation combinations of different 3-dimensional space positions and angles. Preferably most of the fish plows 501 of an agitator are in the lower layer of the volume because movements of the lower layer wastes of the volume can cause movements of the upper layers and these movements of contents in the upper chamber 31 are good enough to make all the contents well aerated. At least one pair of fish plows 501 are in a position near to the side wall of the upper chamber 31 (for example in a position from the draft rod point of no less than ⅔ of the chamber horizontal radius) so that the content along the side wall is well agitated. The frames may be straight or circle of cylinder or horizontally flat metal rod so that it meets with least resistance in moving inside the solid waste. A mould for the fish plow 501 may be added so that it has both the interface to hold a part of the 3-dimensional fish plow 501 and the regular surface to align with surface of the frame. Different sizes of fish plow 501 may be installed on frames of one fish plow agitator.

Figure 6D:
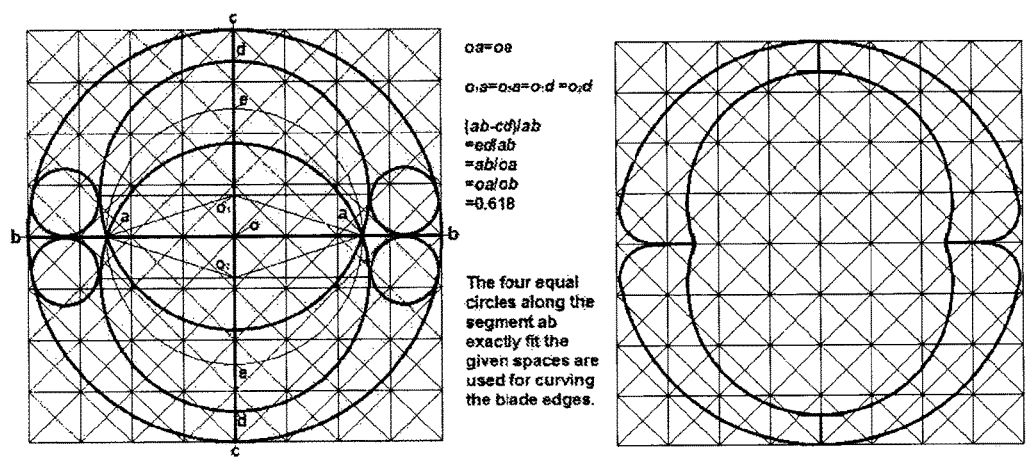
FIG. 6D shows pictures of two prototype samples of the fish plow agitator.

The fish plow 501 is made by bending a fish shape blade metal 3-dimensionally into a plow shape as showing in FIGS. 6A-C.
(1) Based on the FIG. 7C geometry drawing for harvesting the 4 leaf blades of the vortex flower turbine, draw 4 equal circles at the give spaces and make sure the circles pass the outer edges of point a's and point b's.
(2) Harvest 4 fish shape blades by cutting the thicker lines as shown in FIG. 6A.
(3) Point m is the mouth point of the flat fish shape and is the tail point of the fish plow while point t is the tail point of the flat fish shape and is the tip point of the fish plow.
(4) Bending the fish shape blade into a 3-dimensional plow shape and a little further bending than the normal plow blade so that the concaved surface of the fish plow is 3-dimensionally a kind of light "S" type as shown in FIGS. 6B-D.
(5) The blade can be bended in either of the two directions as of its two surfaces therefore producing two kinds of fish plow for either clockwise or anti-clockwise rotation purpose. It meets with less resistance when the concaved surface of a fish plow is to face to the rotation rod than the concaved surface is to face to the side wall of the bioreactor body vessel 11 after it is installed on the frame.
(6) As shown in FIGS. 6C-D, the fish plow is so installed on frames that the tip point t in the front is horizontally much lower than the tail point m in the back.
(7) When the fish plow moves forward along with rotation of the agitator shaft rod, it meets with the least resistance if its axis is in a position perpendicular to the horizontal line between the shaft rod and plow tip t at point t.
(8) The larger of a fish plow the more resistance it meets. The sizes of the fish plow 501 are dependable to the power of motor 60 and the volume of the upper chamber 31. Preferably small sizes (for example the length of the line mt on the flat blade is smaller than 12 inches) of fish plows are employed in the fish plow agitator.

The second embodiment of the present invention is shown in FIG. 2. Preferably, the aeration module 42 comprises of a plurality of airlift pumps 600 so that a vortex swirl circulation in the middle chamber 32 is created, and a specially designed vortex flower turbine 700 shown in FIG. 7A-H is configured to harness the kinetic energy of the vortex swirl. In this configuration, the drain outlet 90 in the middle lowest area of the lower separator 13 is connected into the water pipes 601, 602 of the airlift pumps 600. An outlet 91 from the main water pipe 601 near to the drain 90 is created to introduce liquid into the heating sub-chamber 34 by way of inlet pipe 320. The upper separator 12 is in a higher position so that there is enough volume to hold water for creating the vortex swirling circulation. A plurality airlift pumps 600 are installed from under the lower separator 13 and through to above the lower separator 13. The airlift pump pipes above the lower separator 13 are arranged in the same clockwise or anticlockwise angles so that an vortex swirl circulation is created. Since the vortex swirl in the middle chamber 32 itself agitating the liquid very well, the agitator mechanism 200 of the mixing agitator module 41 inside the middle chamber 32 is therefore omitted.

One of the options to install the air pipes for the airlift pumps is to have a circle pipe with a plurality of T-connectors fixed on the lower surface of the upper separator 12. The air pipe from inlet pipe of the aeration module 42 is connected with the circle pipe. The air pipe for each of the airlift pump 600 is connected with a t-connector on the circle pipe and is installed into the airlift pump 600 for certain depth through the top of the airlift pump 600.

The vortex flower turbine 700 in the middle chamber 32 is connected into the shaft rod 61 of the mixing agitator module 41 with a bearing installed on the upper separator 12 and/or on the lid of vessel 11 to hold the shaft rod 61. In this case, the vortex swirl causes rotation of the turbine 700 in the middle chamber 32 and then rotates the fish plow agitator 62 in the upper chamber 31. The motor 60 used to drive the shaft rod 61 is therefore omitted. A gear box 80 may be added and is installed on and above the lid of vessel 11. It has an inner connector to hold an inner shaft 61 and an outer connector to hold an outer shaft rod 63. It is driven by the inner shaft 61 from rotation of the vortex flower turbine 700 in the middle chamber 32 and it then drives the shaft rod 63 to rotate the fish plow agitator 62 in the upper chamber 31 in a decreased speed and increased torque.

The vortex flower turbine 700 is so named because it looks like a flower and both the flower leaf blades 701 and the channels between the flower leaf blades 701 are of the vortex feature. When the vortex flower turbine 700 is in rotation, swirling of the channels between the flower leaf blades 701 are almost in the same way of the swirling of the vortex current. When the vortex flower turbine 700 is engaged with the vortex swirling current, each of its rotation movement accelerates the swirling current therefore the counterforce and the drag produced are little.

As shown in FIGS. 7B-F, the vortex flower turbine 700 composes of a shaft rod 61 and a plurality of specially drawing leaf blades 701 that are folded around the shaft rod 61 into the vortex flower shape. The narrow ends of the leaf blades 701 are directly fixed on the lower end of the shaft rod 61 while the wide ends are fixed on the shaft rod by way of diameter and circle frames 702. All the leaf blades 701 are properly adjusted so that they are in taut state and the width of the channels are much bigger along the top blade edges than along the bottom blade edges.

Figure 7A:
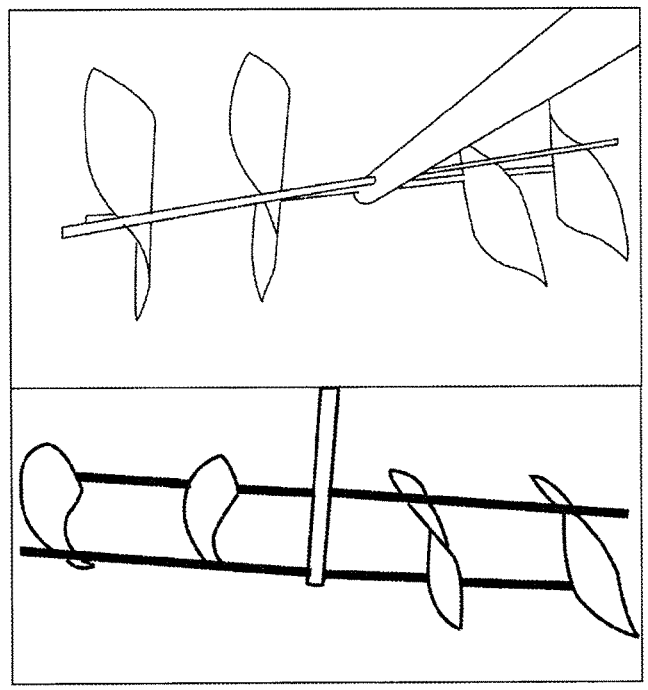
FIG. 7A shows geometry drawings for harvesting 4 leaf blades from a sheet to make a prototype sample of a vortex flower turbine.

FIG. 7A shows geometry drawings to harvest 4 leaf blades 701 from a sheet. Point a divides the radius ob into a golden ratio. Points d is so decided that (ab-cd)/ab=0.618. The circles o1, o2 pass points a and d. The 4 little circles above and below the segments ab are equal and fit the given space exactly. They are used for curving the blade edges. Four leaf blades 701 are harvested by cutting the thicker lines of the drawing in FIG. 7A.

Figure 7B:
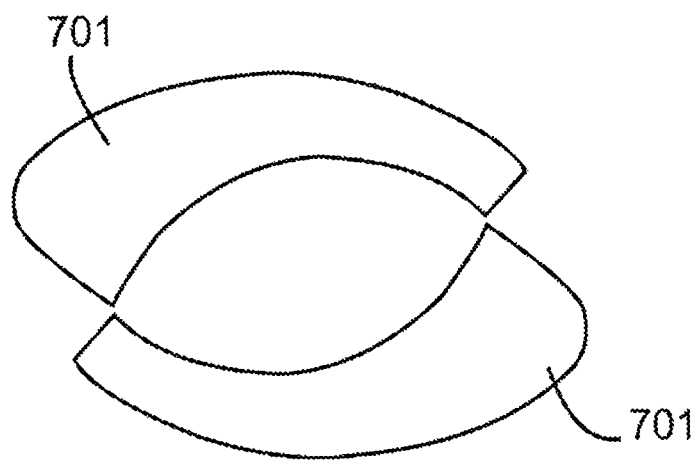
FIGS. 7B-D show method to make a prototype sample of a vortex flower turbine made of 2 leaf blades.
Figure 7C:
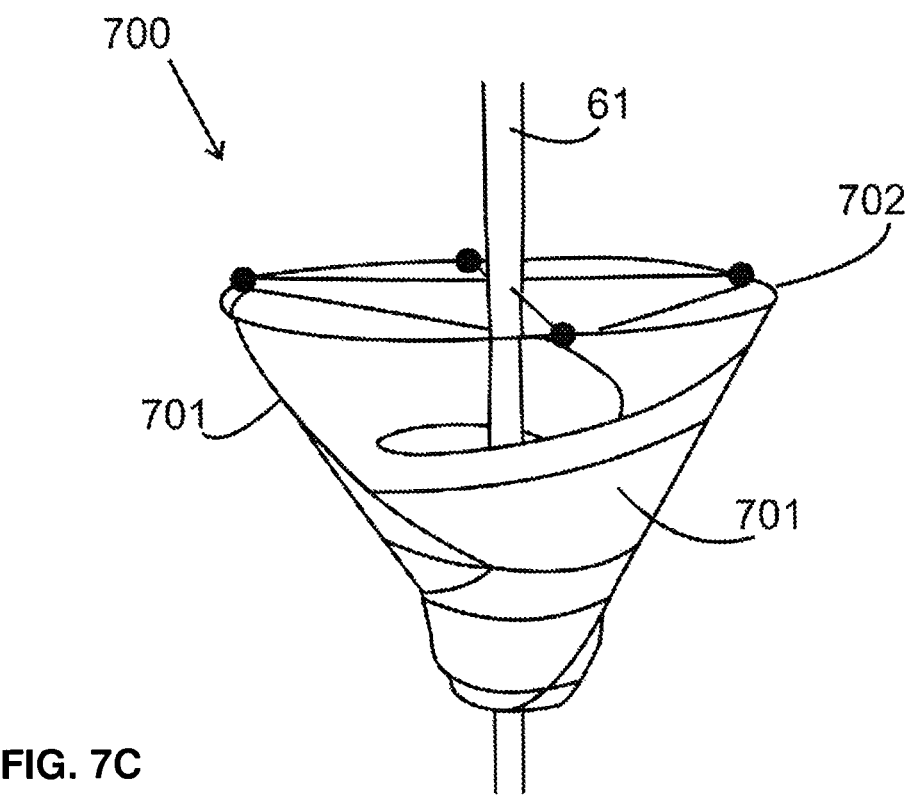
Figure 7D:
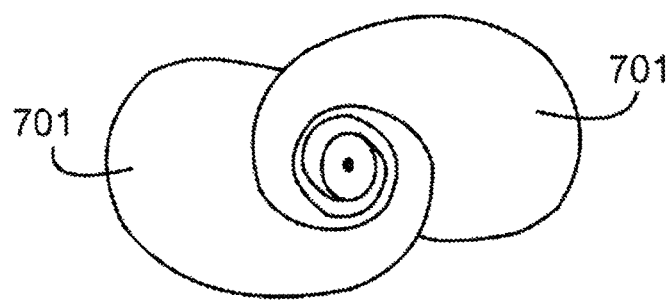
Figure 7E:
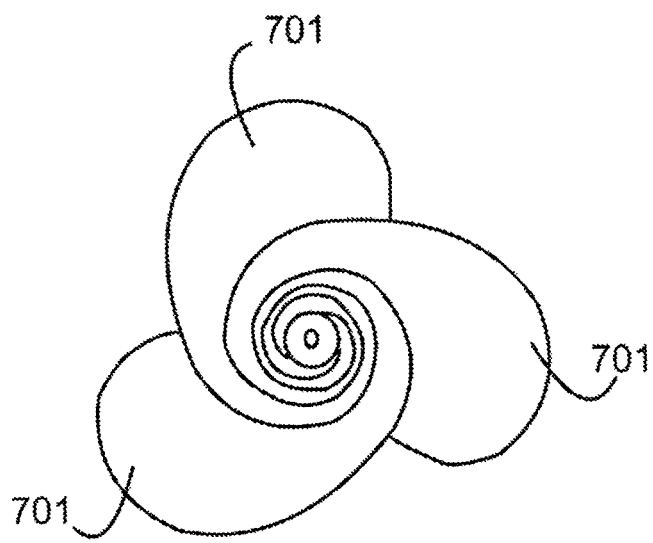
FIG. 7E shows a top view of a prototype sample of a vortex flower turbine made of 3 leaf blades.
Figure 7F:
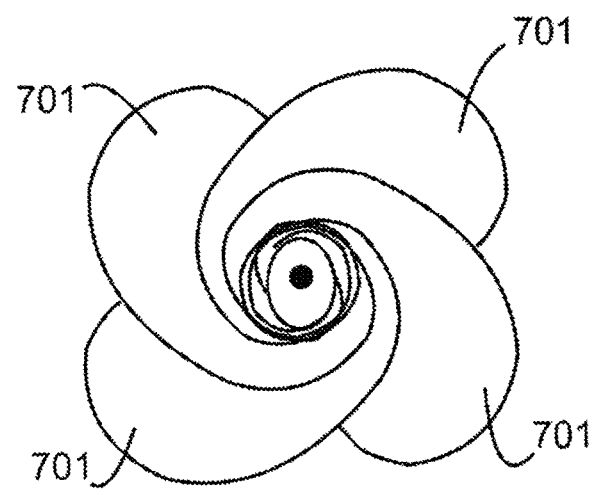
FIG. 7F shows a top view of a prototype sample of a vortex flower turbine made of 4 leaf blades.

FIGS. 7B-D shows the method for making a vortex flower turbine 700 by use of 2 leaf blades 701. FIGS. 7E-F show prototype samples of the vortex flower turbine 700 made either by use of 3 leaf blades 701 or 4 leaf blades 701.

Figure 7G:
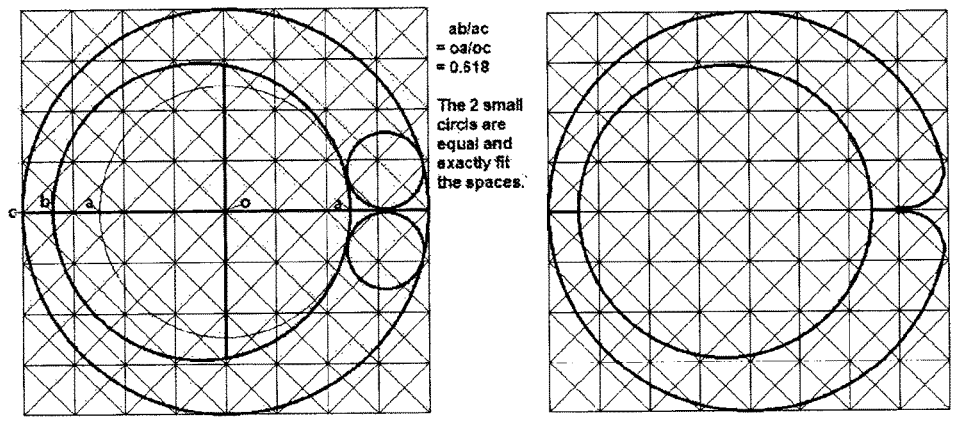
FIG. 7G shows geometry drawings for harvesting 2 leaf blades from a sheet for making a prototype vortex flower turbine.

As shown in FIG. 7G, optionally, another method to make the vortex flower leaf blades is to harvest 2 blades from one sheet. In FIG. 7G, point a is the golden ratio point of radius oc and point b is the golden ratio point of line segment ac where ab/ac=oa/oc=0.618. The circle points of the 3 circles passing points a, b and c are all on segment oc. The two small equal circles exactly fit the given space and are used for curving the blade edges. Since the leaf blades made in this optional method is longer, the vortex flower turbine made by these blades has longer swirl channels between the leaf blades therefore is better in accelerating the swirling current when engaged.

Figure 7H:
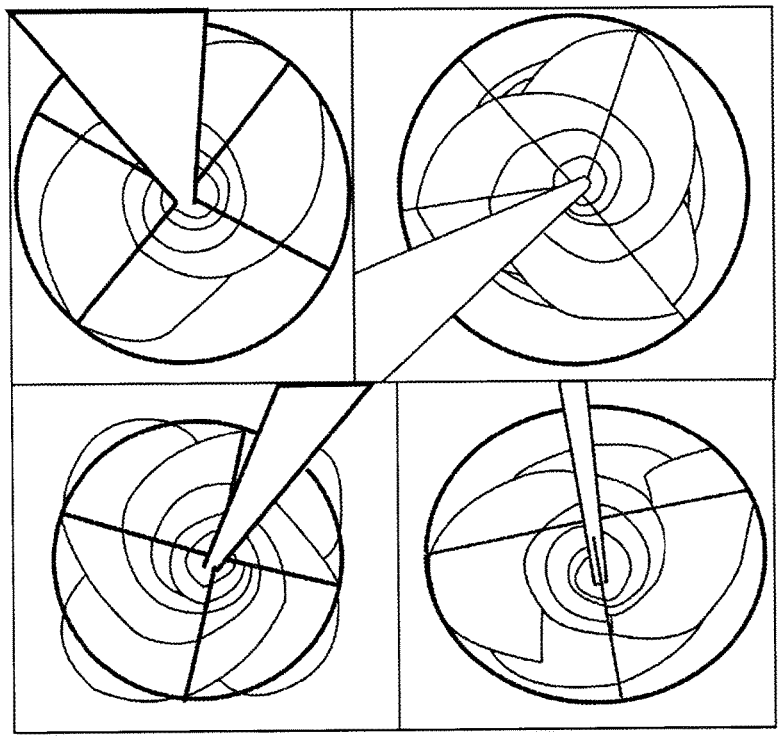
FIG. 7H shows pictures of top view of 4 prototype samples of the vortex flower turbine.

FIG. 7H shows the top view pictures of 4 prototype samples of the vortex flower turbine 700.

The bioreactor body vessel 11 can be any kind of shape of cross-section, preferably it is a cylinder. The height position of the lower separator 13 is so decided that all the components inside the lower chamber 33 can be easily installed. The height position of the upper separator 12 depends on the proportion between solid wastes and waste waters to be treated. The height position of the upper separator 12 is also related to the liquid height position introducing into the extension 100 from the liquid outlet 71. Preferably, when it is configured with the perforated air pipe aeration module as shown in FIG. 1 the upper separator 12 is positioned below the middle point of height of the side wall of the bioreactor body vessel 11 so that the upper chamber 31 has larger volume to hold solid wastes. Preferably, when it is configured with the airlift pump aeration module as shown in FIG. 2 the upper separator is positioned higher so that the middle chamber has enough volume to hold liquid for creation of the vortex swirling.

The air outlet 72, the inlet port of aeration module 42, the waste water inlet(s) 51 and the exhaust gas inlet(s) 52 are positioned on side wall of the upper chamber 31 near to the lid of the bioreactor body vessel 11, so that the inside liquid doesn't reflux to the pipes outside the body vessel 11. The inside pipe connected with the exhaust gas inlet(s) 52 is turned down and pass through the upper separator 12 to reach inside the middle chamber 32. Preferably the part of the pipe near to the exit is fixed on the lower surface of the upper separator 12 or the side wall of the middle chamber 32 so that less noise is produced inside when the exhaust gas is driven by a duct fan.

Optionally, a part of the side wall in the upper chamber 31 may be a sealed gate or an openable mechanism so that the upper chamber 31 can be accessible from outside, in case it is required to remove the residue humus that is unbreakable. Also, a portion of the lid or the side wall of the bioreactor body 11 may be transparent so that the inside space can be seen and monitored from outside.

Figure 4:
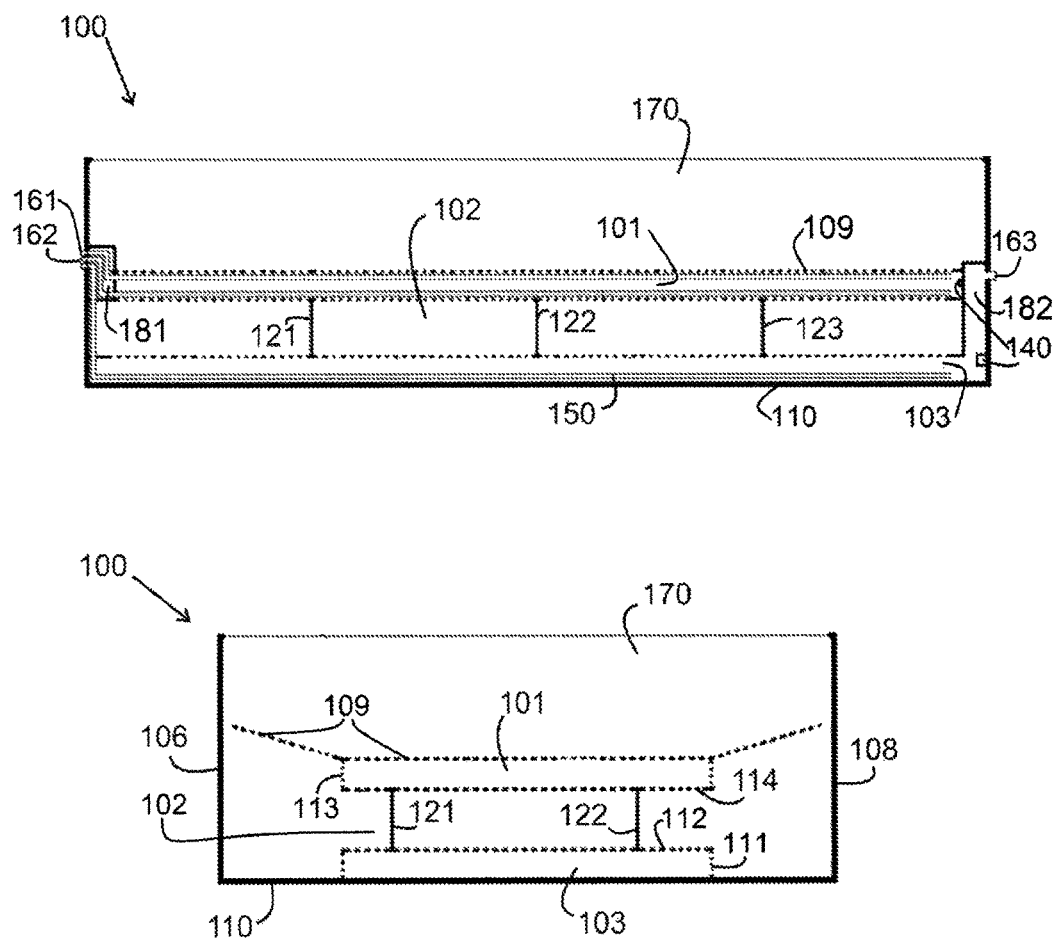
FIG. 4 shows a sectional elevation and a cross-sectional elevation of the extension.

As shown in FIG. 4, the extension 100 comprises of three channels 101-103 that are the upper channel 101, the middle channel 102 and the lower channel 103. Preferably, the middle channel 102 extends up and down along the side walls 106, 108, so that it reaches to the bottom wall 110 and the top wall 109. The parts of the top wall 109 near to the side walls 106, 108 are of open style so that bio-filter media such as lightweight expanded clay aggregate (LECA) or other medias can be loaded into the middle channel 102. The top wall 109 and the separator boards 111-114 between the channels 101-103 are all perforated to allow liquid filter through. Preferably the extension 100 shares with the wicking bed for the side walls 106, 108 and the bottom wall 110 and some vertical support frames 121-123 are added between the separator boards 112 and 114. At least one temperature sensor 140 is installed in each of the upper channel 101 and the lower channel 103 and is connected into the central control unit 20. An aeration module 150 is installed inside the lower channel 103. Both the liquid outlet 71 and the air outlet 72 from the bioreactor body 10 are introduced into the chamber of the upper channel by way of the liquid inlet 161 and air inlet 162. Preferably, all the water pipes and aeration pipes in the extension are in the sinuous path style to enhance the inside water circulations.

At the extension end near to the bioreactor body 10, a chamber 181 is separated so that it can only connect into the upper channel 101. At the extension end far from the bioreactor body 10, a chamber 182 is separated so that it can only connect into the lower channel 103. In the chamber 182 of the far end, there is either an outlet 163 in the level of the upper channel 101 or a syphon to let go the liquid from the extension 100. When the syphon is employed, the syphon off level to stop liquid flowing is set near to the bottom of the lower channel. Since air goes into inside of the channels during the liquid flowing out from the syphon, the aeration module 150 in the lower channel 103 is therefore omitted.

The extension 100 is to stay inside at the lower layer of a wicking bed 170 and to work as the water reservoir of the wicking bed 170. Top soil or compost or other media of 8-12 inches of thickness or other thicknesses is added in the wicking bed 170. Worms such as *eisenia fetida* or other species are cultured in the wicking bed 170. The extension 100 supplies water, oxygen, nutrients, microorganisms and heat from lower layer to top layer of the wicking bed to grow worms and food plants. The worms are harvested for feeding the aquaculture animals of the integrated aquaponics system.

When the stove unit 30 is employed, the bottom of the bioreactor body vessel 11 is made of thermally conductive material and is not insulated. The stove unit 30 is a wood stove which has a heat radiator structure 300 positioned underneath the bioreactor body vessel 11 working as its support base. Preferably it is made of clay and fire brick and its side wall has an insulation outer layer so that it can hold heat in high temperature for a long time to heat the bioreactor body vessel 11. Preferably the stove unit 30 has the feature of secondary combustion to increase efficiency. Optionally, an auto control module may be added to control combustion according to temperatures monitored by use of mechanisms that can automatically feed fire woods into the combustion chamber and adjust the stove damper.

The chimney vent 301 of the stove unit 30 is introduced into the exhaust gas inlet 52 of the bioreactor body vessel 11 and an duct fan may be added to drive the exhaust gases into the vessel 11.

The extension 100 and all the components inside the extension 100 and inside the bioreactor body vessel 11 are made of materials that are corrosion resistant and high temperature (for example 100° C. and up) resistant. When the stove unit 30 is employed, the bottom and side wall(s) of the bioreactor body vessel 11 inner tank are made of steel or other metals that are treated for corrosion resistant and are high temperature (for example 800° C. and up) resistant.

The size of the bioreactor body vessel 11 and the size of the extension 100 are proportionally arranged and dependable to the volume of biodegradable wastes to be treated. One bioreactor body 10 and one extension 100 are normally installed for one site, however it is also optional to have two or more bioreactor bodies 10 and two or more extensions 100 in one site. When two or more extensions are serially installed with one bioreactor body 10, the first extension 100 near to the bioreactor body 10 have an liquid outlet 163 in the far end chamber 182 to connect into the liquid inlet 161 of the next extension 100, and the last extension 100 far to the bioreactor body 10 have an syphon in the far end chamber 182 to let go the liquid.

Preferably, the diameter of the bioreactor body vessel 11 and width of the extension 100 match with each other. For a wicking bed a width of 4-5 feet is good for operations if it is reachable from both sides while a width of 2-3 feet is good for operations if it is reachable from only one side.

One of the options for the heights of the bioreactor body vessel 11 is in the range of 2.5 feet to 4 feet so that when the body vessel 11 sits on the stove radiator 300 the total height from top of the feed module 44 to the ground is about 4-6 feet, a proper height reachable for most persons to feed wastes.

One of the options for the heights of the extension 100 is 12 inches so that it has a height space of around 3-4 inches for both the upper channel 101 and the lower channel 103 that allows easy installation of the aeration and water pipes while it has a height space of around 4-6 inches that is good to hold enough bio-filter media.

Optionally, a thermoelectric generator module may be integrated into the stove unit 30 so that it generates electricity to power the electronic components of the stove unit and the bioreactor system from the temperature differences between the side contacting with the stove wall (a part without the insulation layer) and the opposite side.

Optionally, a microbial fuel cell (MFC) stack module may be added both inside the bioreactor body vessel 11 and inside the middle channel 102 of the extension 100. The MFCs may be connected serially and/or in parallel to generate electricity in required voltage and current values. The conditions inside the bioreactor system are beneficial for MFCs to generate electricity while the processes of MFCs generating electricity are beneficial for the liquid to be further decomposed. Electricity generated by the MFC stack modules may be used to heat the inside liquid by installing an electric resistance wire within the circuit, and/or may be used by the electric components of the system.

Inside the bioreactor body vessel, the space above the upper surface of the conical or concaved separator 13 is with aerobic condition because of the aeration module 42, while the space under its lower surface is with anaerobic condition because of the higher temperature in the lower chamber, oxygen is driven out either through the liquid outlet 71 to the extension 100 or through the heat sub-chamber inlet pipe 320 into the middle chamber 32. The aerobic condition fits for the MFC cathode while the anaerobic condition fits for the MFC anode. Therefore, the conical or concaved lower separator 13 may be constructed by installing a plurality of MFCs on bone frames with the cathodes as the upper surface and anodes as the lower surface.

Inside the extension, the space area above the separate board 112 between the middle channel 102 and the top of the lower channel 103 may be created, and/or the space areas outside the separate board 111 between the middle channel 102 and the sides of the lower channel 103 may be created, so that the top surface and/or the side surfaces faced to the lower channel 103 are with aerobic condition because of the aeration module 150 inside the lower channel 103 while the opposite surfaces are with anaerobic condition because of physical separation. Therefore, MFC stacks may be constructed with the anodes in the anaerobic surface areas and the cathodes in the aerobic surface areas.

Preferably a grinder module may be employed to grind the kind solid wastes such as shells, bones and etc. having unbreakable residue humus into fine particles and liquids, therefore to speed the composting processes and to supply bio-mineral nutrients into the integrated food growing system. Optionally, for embodiments using large size of bioreactor body vessels, more than one feed module 44 and more than one mixing agitator modules 41 (if driven by the motor 60) may be employed in each bioreactor body vessel.

The central control unit 20 is installed nearby the bioreactor body 10 or other places, preferably it is installed on the side wall or on top of the lid of the bioreactor body vessel 11. It reads and displays all the data from the sensors both inside the bioreactor body vessel 11 and inside the extension 100. It automatically controls the mixing agitator module 41, the aeration module 42 and the heat module 43 to turn them on/off according to pre-set conditions and/or monitored data of inside conditions. Preferably, the central control unit 20 has an interface to connect into the Wi-Fi or cellular modem or other network communication system, so that the monitored data of the central control unit 20 can be reached by a specially designed application that runs on smart phones, tablets and other devices.

Preferably, the liquid inside the extension 100 is tested and monitored regularly for PH and chemical components. In certain conditions, the plants that are good to degrade the monitored chemicals by rhizofiltration and phytoremediation are employed to grow in the extension wicking bed(s).

Figure 8:
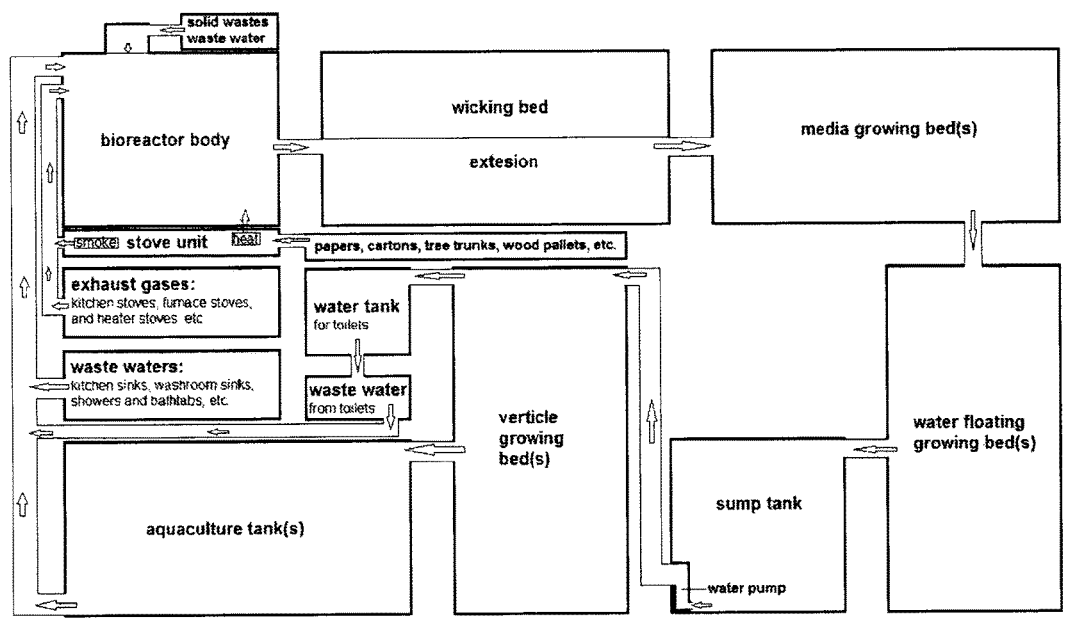
FIG. 8 shows the flow chart of a typical embodiment.

As show in FIG. 8, a closed loop circulation can be reached for an integrated system both for foods growing and for wastes recycling based on a typical embodiment of this invention.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A bioreactor system for recycling biodegradable wastes, comprising:
    a. a bioreactor vessel having a vessel volume, said volume is divided into an upper chamber to receive said biodegradable wastes, a middle chamber to receive a filtered biodegradable waste generated in the upper chamber, and a lower chamber to receive a liquid waste generated in the middle chamber;
    b. a perforated plate separator to separate said upper chamber and said middle chamber and a concaved or a conical separator to separate middle chamber from said lower chamber;
    c. a fish plow mixing agitator module installed in the upper chamber to provide a harmonized mixing;
    d. an oblique cone mixing agitator module installed in the middle chamber to provide a harmonized mixing;
    e. an aeration module installed in the middle chamber, said aeration module comprises of a plurality of perforated pipes fixed on an upper surface of said concaved or conical lower separator;
    f. a heating module installed in the lower chamber to heat said liquid waste and kill pathogen microbes and weed seeds of said liquid waste;
    g. an extension having an upper volume, a middle volume filled with a bio-filter media and having means to receive said liquid waste from said lower chamber, and a lower volume having a second aeration module;
    h. a plurality of inlet and outlet ports;
    i. a plurality of sensors for temperature, humidity, oxygen, ammonia, carbon dioxide and air pressure installed inside the bioreactor vessel and connected to a central control unit, said sensors generating sensor-data; and
    j. said central control unit to control said modules for heating, aeration and agitation in said system,
        whereby said system provides a created condition to speed up degrading said biodegradable waste into a usable liquid in a continuous manner.

2. The bioreactor system of claim 1, wherein said bioreactor vessel further having a top lid and a feed module on said top lid to feed said biodegradable wastes into said upper chamber.

3. The bioreactor system of claim 1, wherein said system further having at least one waste water liquid inlet port feeding into said upper chamber.

4. The bioreactor system of claim 1, wherein said lower chamber comprising a heating-sub-chamber, wherein said heating-sub-chamber having a heating module to heat the content of said heating-sub-chamber to kill pathogen microbes and weed seeds of a waste water flowing through said heating-sub-chamber to generate a heated waste water, and a collection chamber to collect said heated waste water from the heating sub-chamber and to moderate the temperature of the heated waste water.

5. The bioreactor system of claim 4, wherein a temperature inside said heating-sub-chamber is between 70-100° C.

6. The bioreactor system of claim 1, wherein said oblique cone agitator in said middle chamber is made by installing a plurality of oblique cones on a circle frame or circle frames together composing horizontal and/or vertical layers of which lower layer is smaller than upper layer to fit for the concaved or conical shape of said lower separator.

7. The bioreactor system of claim 1, further having a stove unit which has a heat radiator structure, wherein said radiator structure is positioned underneath the bottom of the bioreactor body vessel and also works as support base of said body vessel, wherein said stove unit is a wood stove that has a heat radiator structure made of clay and fire brick, and its side walls has an insulation outer layer to hold heat in high temperature for a long time to heat the bioreactor body vessel.

8. The bioreactor system of claim 1, further having a stove unit to heat said bioreactor vessel and said extension by a combustion process of a and wherein said stove unit has a chimney vent that introduces combustion exhaust gases into the inlet of the bioreactor body vessel and a duct fan may be added to drive the exhaust gases into the vessel.

9. The bioreactor system of claim 1, wherein said central control unit reads and displays said sensor-data from the sensors both inside the bioreactor vessel and the extension, controls the mixing agitator module, the aeration module and the heating module to turn on/off according to a pre-set condition.

10. The bioreactor system of claim 1, wherein the extension further having a wicking bed filled with a soil or a compost or other media of 8-12 inches of thickness with *Eisenia fetida* to be cultured in the wicking bed.

11. The bioreactor system of claim 1, wherein said perforated plate separator has a plurality of perforations, wherein each said perforation has a diameter in the range of ½-¼ inch.

12. The bioreactor system of claim 1, wherein said bio-filter media in the extension is a lightweight expanded clay aggregate (LECA).

13. A bioreactor system for recycling biodegradable wastes, comprising:

a. a bioreactor vessel having a vessel volume, said volume is divided into an upper chamber to receive said biodegradable wastes, a middle chamber to receive a filtered biodegradable waste generated in the upper chamber, and a lower chamber to receive a liquid waste generated in the middle chamber;

b. a perforated plate separator to separate said upper chamber and said middle chamber and a concaved or a conical separator to separate middle chamber from said lower chamber;

c. a fish plow mixing agitator module installed in the upper chamber to provide a harmonized mixing;

d. an vortex flower turbine mixing agitator module installed in the middle chamber to provide a harmonized mixing and necessary torque for driving said fish plow mixing agitator module;

e. an aeration module installed in the middle chamber, said aeration module comprises of a plurality of airlift pumps to generate a swirling vortex in the middle chamber;

f. a heating module installed in the lower chamber to heat said liquid waste and kill pathogen microbes and weed seeds of said liquid waste;

g. an extension having an upper volume, a middle volume filled with a bio-filter media and having means to receive said liquid waste from said lower chamber, and a lower volume having a second aeration module;

h. a plurality of inlet and outlet ports;

i. a plurality of sensors for temperature, humidity, oxygen, ammonia, carbon dioxide and air pressure installed inside the bioreactor body vessel and connected into a central control unit; and j. a central control unit to control said modules for heating, aeration and agitation in said system, whereby said system provides a created condition to speed up degrading said biodegradable waste into a usable liquid in continuous manner.

14. The bioreactor system of claim 13, further having a specially designed vortex flower turbine installed in the middle chamber and connected into the shaft rod of the mixing agitator module with a bearing installed on the upper separator and/or the lid of said body vessel to hold the shaft rod, whereby the vortex swirl causes rotation of the vortex flower turbine in the middle chamber which drives to rotate the fish plow agitator in the upper chamber, wherein said vortex flower turbine is made by fixing and folding a plurality of flower leaf blades on and around a shaft rod so that both the edges of the flower leaf blades and the channels between the flower leaf blades are in a vortex feature shape.

* * * * *